United States Patent [19]

Klaus et al.

[11] Patent Number: 5,106,981
[45] Date of Patent: Apr. 21, 1992

[54] STILBENE DERIVATIVES

[75] Inventors: Michael Klaus, Weil am Rhein; Peter Mohr, Basle; Ekkehard Weiss, Inzlingen, all of Fed. Rep. of Germany

[73] Assignee: Hoffmann-La Roche Inc., Nutley, N.J.

[21] Appl. No.: 510,705

[22] Filed: Apr. 19, 1990

Related U.S. Application Data

[62] Division of Ser. No. 310,442, Feb. 14, 1989, Pat. No. 4,940,707.

[30] Foreign Application Priority Data

Feb. 24, 1988 [CH] Switzerland ............................ 689/88
Dec. 14, 1988 [CH] Switzerland ........................ 4622/88

[51] Int. Cl.$^5$ ............................................. C07D 409/00
[52] U.S. Cl. ................................... 546/195; 546/184; 546/192
[58] Field of Search ..................... 546/195, 192, 184; 514/277, 279

[56] References Cited

U.S. PATENT DOCUMENTS

| | | |
|---|---|---|
| 3,437,607 | 4/1969 | Nashu et al. |
| 3,483,209 | 12/1969 | Mizzoni |
| 3,630,680 | 12/1971 | Rittersdorf et al. |
| 4,369,310 | 1/1983 | Postle |
| 4,396,553 | 8/1983 | Klaus et al. |
| 4,422,969 | 12/1983 | Beecken |
| 4,870,219 | 9/1989 | Klaus et al. |
| 4,935,560 | 6/1990 | Klaus et al. |

FOREIGN PATENT DOCUMENTS

| | | |
|---|---|---|
| 641160 | 12/1963 | Belgium |
| 544087 | 2/1932 | Denmark |
| 3602473 | 7/1987 | Denmark |
| 0004066 | 9/1979 | European Pat. Off. |
| 058370 | 8/1982 | European Pat. Off. |
| 87/3244 | 5/1987 | South Africa |
| 502301 | 1/1971 | Switzerland |
| 456534 | 12/1936 | United Kingdom |

OTHER PUBLICATIONS

Chemical Abstracts 67(17):81885a (1967).
Chemical Abstracts 70(9):834723y (1968).
Chemical Abstracts 87: 69720y (1977).
Chemical Abstracts 76: 127329p (1972).
Chemical Abstracts 107: 87107q (1987).
Naruto et al., Synthesis and Spasmolytic Activity of 2-substituted-3-(w-di-alkylaminoalkoxyphenyl)a-crylonitriles and Related Compounds, Chem. Pharm. Bull., 31(6) pp. 2023-2032 (1983).
Weygand-Hilgetag, Experimental Methods in Organic Chemistry Moscow (pp. 333, 413 and 584 (1968)).
Loeliger et al., Arotinoids, a new class of highly active retinoids, Eur. J. Med. Chem-Chimica Therapeutica, Jan.-Feb., pp. 9-15 (1980).

*Primary Examiner*—Marianne Cintins
*Assistant Examiner*—Jessica H. Nguyen
*Attorney, Agent, or Firm*—George M. Gould; William G. Isgro; Ellen Ciambrone Coletti

[57] ABSTRACT

Compounds of the formula

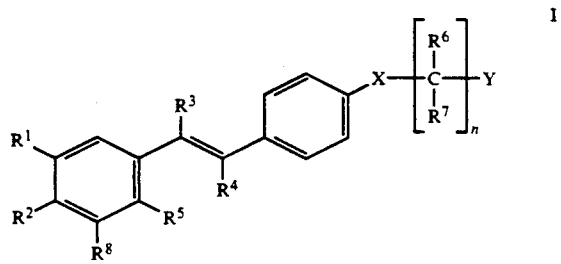

wherein $R^1$ and $R^2$ each independently are lower-alkyl; or together are alkylene with 3-5 C-atoms in a straight chain; one of the residues $R^3$ and $R^4$ is hydrogen and the other is hydrogen or lower-alkyl; $R^6$ and $R^7$ are hydrogen or lower-alkyl; $R^5$ and $R^8$ are hydrogen, lower-alkyl, lower-alkoxy or halogen; X signifies —O—, —S—, —SO—, —SO$_2$— or —NR$^9$; $R^9$ is hydrogen, lower-alkyl or acyl; Y is —S(O)$_m$R$^{10}$ or —NHet and, where X is —NR$^9$—, —S—, —SO— or —SO$_2$—, also —N(R$^{11}$)$_2$ or —OR$^{12}$; $R^{10}$ is lower-alkyl; $R^{11}$ and $R^{12}$ are hydrogen, lower-alkyl or acyl; —NHet is a 5-8 membered, saturated or unsaturated, monocyclic heterocycle attached via a N-atom; n is 2, 3 or 4 and m is 0, 1 or 2, are described. The compounds of formula I are useful as agents for the treatment of disorders such as neoplasms, dermatoses or ageing of the skin.

7 Claims, No Drawings

STILBENE DERIVATIVES

This is a division of application Ser. No. 07/310,442, filed Feb. 14, 1989, now U.S. Pat. No. 4,940,707.

BRIEF SUMMARY OF THE INVENTION

The invention relates to stilbene derivatives of the formula

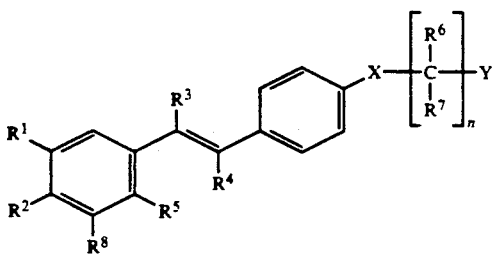

wherein $R^1$ and $R^2$ each independently is lower-alkyl; or together are alkylene with 3-5 C-atoms in a straight chain; one of the residues $R^3$ and $R^4$ is hydrogen and the other is hydrogen or lower-alkyl; $R^6$ and $R^7$ are hydrogen or lower-alkyl; $R^5$ and are hydrogen, lower-alkyl, lower-alkoxy or halogen; X is —O—, —S—, —SO—, —SO$_2$— or —NR$^9$; $R^9$ is hydrogen, lower-alkyl or acyl; Y is —S(O)$_m$R$^{10}$ or —NHet and, where X is —NR$^9$—, —S—, —SO— or —SO$_2$—, also —N(R$^{11}$)$_2$ or —OR$^{12}$; $R^{10}$ is lower-alkyl; $R^{11}$ and $R^{12}$ are hydrogen, lower-alkyl or acyl;. —NHet is a 5-8 membered, saturated or unsaturated, monocyclic heterocycle attached via a N-atom; n is 2, 3 or 4 and m is 0, 1 or 2.

The compounds of formula I, are useful as agents in the treatment and prophylaxis of neoplasms, dermatoses and ageing of the skin.

DETAILED DESCRIPTION OF THE INVENTION

The invention relates to stilbene derivatives of the formula

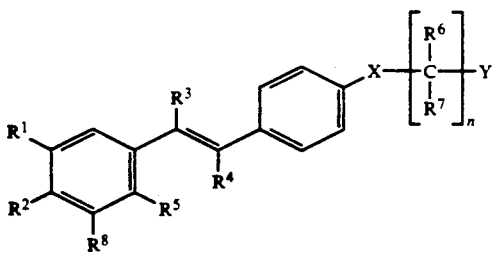

wherein $R^1$ and $R^2$ each independently is lower-alkyl; or together are alkylene with 3-5 C-atoms in a straight chain; one of the residues $R^3$ and $R^4$ is hydrogen and the other is hydrogen or lower-alkyl; $R^6$ and $R^7$ are hydrogen or lower-alkyl; $R^5$ and $R^8$ are hydrogen, lower-alkyl, lower-alkoxy or halogen; X is —O—, —S—, —SO—, —SO$_2$— or —NR$^9$; $R^9$ is hydrogen, lower-alkyl or acyl; Y is —S(O)$_m$R$^{10}$ or —NHet and, where X is —NR$^9$—, —S—, —SO— or —SO$_2$—, also —N(R$^{11}$)$_2$ or —OR$^{12}$; $R^{10}$ is lower-alkyl; $R^{11}$ and $R^{12}$ are hydrogen, lower-alkyl or acyl; —NHet is a 5-8 membered, saturated or unsaturated, monocyclic heterocycle attached via a N-atom; n is 2, 3 or 4 and m is 0, 1 or 2.

Furthermore, the invention is concerned with a process for the preparation of the compounds of formula I, pharmaceutical preparations based on the compounds of formula I, the compounds of formula I in the treatment and prophylaxis of neoplasms, dermatoses and ageing of the skin as well as the use of the compounds of formula I in the manufacture of pharmaceutical preparations for the treatment and prophylaxis of such disorders.

The term "lower" relates to groups with 1-6 C-atoms. Alkyl and alkoxy groups can be straight-chain or branched, such as methyl, ethyl, propyl, isopropyl, butyl, sec.-butyl or tert.-butyl and methoxy, ethoxy, propoxy, isopropoxy, butoxy, sec.-butoxy and tert.-butoxy, respectively. Examples of acyloxy groups are alkanoyloxy groups, preferably lower-alkanoyloxy groups such as acetoxy, propionyloxy, butyryloxy, pivaloyloxy and caproyloxy; or aroyloxy groups such as benzoyloxy, p-nitrobenzoyloxy and toluoyloxy; or aralkanoyloxy groups such as phenylacetoxy. Halogen embraces fluorine, chlorine, bromine and iodine. Preferred heterocyclic residues —NHet are those of the formula $$-NY'$$

in which Y' is —CH$_2$—, —CH=, —O—, —S—, —SO—, —SO$_2$— or —NR$^{13}$— and $R^{13}$ is hydrogen, lower-alkyl or acyl and wherein a total of 3-6 C-atoms are disposed between N and Y'. Examples of such residues are piperidino, pyrrolidino, morpholino, piperazino, N-methylpiperazino, thiomorpholino, thiomorpholino 4-oxide, thiomorpholino 4,4-dioxide as well as imidazolino and pyrrolo. When $R^1$ and $R^2$ is an alkyl residue with 3-5 C-atoms in a straight chain, said residue can be lower alkyl substituted. Examples of such alkylene residues are 1,3-propylene, 1,4-butylene and 1,5-pentylene and lower-alkyl-substituted derivatives thereof such as the residues —C(CH$_3$)$_2$—CH$_2$—C(CH$_3$)$_2$—, —C(CH$_3$)$_2$—CH$_2$CH$_2$—C(CH$_3$)$_2$—and —CH$_2$CH$_2$—C(CH$_3$)$_2$—CH$_2$CH$_2$—.

The compounds of formula I can be present as trans or cis isomers or cis/trans isomer mixtures. In general, the trans compounds of formula I are preferred.

preferred groups of compounds of formula I are those in which $R^1$ and $R^2$ together are a residue —C(CH$_3$)$_2$—CH$_2$—C(CH$_3$)2— or —C(CH$_3$)$_2$—CH$_2$—C(CH$_3$)$_2$—; $R^4$, $R^5$ and $R^8$ are hydrogen; and $R^3$ is methyl. Furthermore, the compounds of formula I in which $R^1$ and $R^8$ are lower-alkyl, especially tert.-butyl, are of particular interest. Further, the compounds of formula I in which X is —O—and Y is —NHet, such as 4-[2-[p-[(E)-2-(5,6,7,8-tetrahydro-5,5,8,8-tetramethyl-2-naphthyl)propenyl]phenoxy]ethyl]morpholine, are preferred.

Furthermore, compounds of formula I in which X is —S—, —SO—, —SO$_2$—or —NR$^9$ and Y is —S(O)$_m$R$^{10}$ or —NHet are of particular interest.

Typical representatives of the compounds in accordance with the invention are the compounds described in the Examples as well as the compounds listed hereinafter:

4-[2-[p-[(E)-2-(5,6,7,8-Tetrahydro-5,5,8,8-tetramethyl-2-naphthyl)propenyl]anilino]ethyl]morpholine;

4-[2-[[p-[(E)-2-(5,6,7,8-tetrahydro-5,5,8,8-tetramethyl-2-naphthyl)propenyl]phenyl]thio]ethyl]morpholine;

1-methyl-4-[2-[p-[(E)-2-(5,6,7,8-tetrahydro-5,5,8,8-tetramethyl-2-naphthyl)propenyl]phenoxy]ethyl]piperazine;

cis-2,6-dimethyl-4-[2-[p-[2-(E)-5,6,7,8-tetrahydro-5,5,8,8-tetramethyl-2-naphthyl]propenyl]phenoxy]ethyl]morpholine;

tetrahydro-4-[2-[p-[(E)-2-(5,6,7,8-tetrahydro-5,5,8,8-tetramethyl-2-naphthyl)propenyl]phenoxy]ethyl]-2H-1,4-thiazine;

tetrahydro-4-[2-[p-[(E)-2-(6,7,8,9-tetrahydro-7,7-dimethyl-5H-benzocyclohepten-2-yl)propenyl]anilino]ethyl]-2H-1,4-thiazine;

5,6,7,8-tetrahydro-5,5,8,8-tetramethyl-5,5,8,8-tetramethyl-2-naphthyl]propenyl]phenoxy]ethyl]pyrrole;

1-[2-[p-[(E)-2-(5,6,7,8-tetrahydro-5,5,8,8-tetramethyl-2-naphthyl)propenyl]phenoxy]ethyl]imidazole.

The compounds of formula I can be obtained in accordance with the invention by a) reacting a compound of the formula

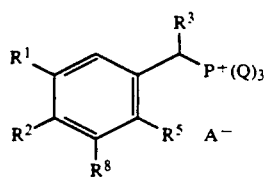

II with a compound of the formula

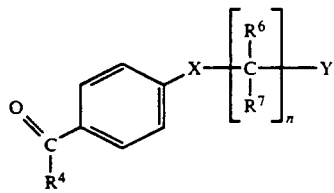

III b) reacting a compound of the formula

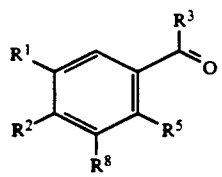

IV with a compound of the formula

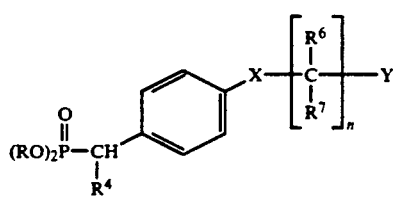

V c) reacting a compound of the formula

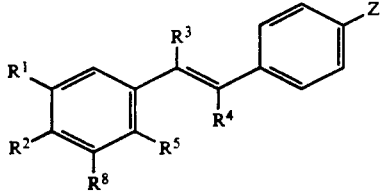

VI with a compound of the formula

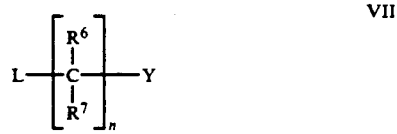

VII and, if desired, oxidizing a sulphide group represented by X and/or Y in a thus-obtained compound of formula I to a sulphoxide or sulphone group, wherein in the foregoing formulae II–VII $R^1$, $R^2$, $R^3$, $R^4$, $R^5$, $R^6$, $R^7$, $R^8$, X, Y and n are as described above; Q is aryl; A is an anion of an inorganic or organic acid; R is a lower alkyl group; Z is hydroxy, mercapto, $-NHR^9$ or $-SO_2-M^+$; $M^+$ is a cation; and L is a leaving group.

The reaction in accordance with process variant a) can be carried out under the usual process conditions of a Wittig reaction. Thereby, the components are reacted with one another in the presence of an acid-binding agent, e.g. in the presence of a strong base such as e.g. butyllithium, sodium hydride, potassium tert.-butylate or the sodium salt of dimethyl sulphoxide, but especially in the presence of an ethylene oxide which is optionally substituted by lower alkyl such as 1,2-butylene oxide, optionally in a solvent, e.g. in an ether such as diethyl ether or tetrahydrofuran or in an aromatic hydrocarbon such as benzene or toluene, in a temperature range lying between room temperature and the boiling point of the reaction mixture.

Of the inorganic acid ions $A^-$ the chloride and bromide ion or the hydrosulphate ion is preferred and of the organic acid ions the tosyloxy ion is preferred. The aryl residue Q is preferably a phenyl residue or a substituted phenyl residue such as p-tolyl.

The reaction according to process variant b) can be carried out under the usual conditions of a Horner reaction. Thereby, the components are condensed with the aid of a base and preferably in the presence of an inert organic solvent, e.g. with the aid of sodium hydride in benzene, toluene, dimethylformamide, DMSO, tetrahydrofuran, dioxan or 1,2-dimethoxyethane, or also with the aid of a sodium alcoholate in an alkanol, e.g. sodium methylate in methanol, in a temperature range lying between 0° and the boiling point of the reaction mixture.

The alkoxy residues RO are preferably lower alkoxy residues with 1–6 carbon atoms such as methoxy or ethoxy.

The reaction according to process variant c) can be carried out in an organic solvent such as dimethylformamide, conveniently while heating up to the reflux temperature of the reaction mixture. Examples of leaving groups L are halogen such as chlorine; mesyloxy and tosyloxy The cation $M^+$ in a compound of formula VI is conveniently an alkali metal cation such as Na+ or K+; or NH4+.

The oxidation of a sulphide group X or Y to a sulphoxide group and the oxidation of a sulphoxide group X or Y to a sulphonyl group can be carried out with oxidation agents such as peracids, e.g. Peracetic acid or m-chloroperbenzoic acid. The oxidation of a sulphide group to the sulphoxide group can also be effected by means of periodates such as sodium periodate.

The starting materials of formulae II–VII, insofar as they are not known or described herein, can be prepared in anology to known methods or methods decribed herein.

Compounds of formulae II and IV and their preparation are described e.g. in German Offenlegungsschriften 2 414 619 and 2 819 213 and European patent Specification 2742.

Compounds of formula III can be prepared starting from p-hydroxy-, p-mercapto-, p-amino-, p-alkylamino- or p-acylamino-substituted benzaldehydes or acetophenones, propiophenones or homologues thereof by reaction with a compound of the formula Y(CR$^6$,R$^7$)$_n$Cl in the presence of a base such as NaH or by reacting a p-halo-benzaldehyde with an amine of the formula NHR$^9$—(CR$^6$,R$^7$)$_n$Y or a mercaptan of the formula HS—(CR$^6$,R$^7$)$_n$Y in the presence of a base such as K$_2$CO$_3$.

Compounds of formula V can be prepared starting from p-hydroxy-, p-mercapto- or p-amino-, alkylamino- or acylamino-substituted benzoic acid esters by reaction with a compound of the formula Y(CR$^6$,R$^7$)$_n$Cl, reduction of the ester group with Dibal or LiAlH$_4$ to the corresponding alcohol, replacement of the hydroxy group by bromine, e g by reaction with pBr$_3$, and reaction of the bromide with a trialkyl phosphite to give a phosphonate of formula V.

Compounds of formula VI wherein Z is hydroxy can be prepared from compounds of formula II and compounds of the formula

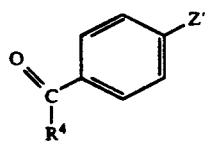

VIII wherein Z' is a protected hydroxy group, e.g. an acetoxy group or tetrahydropyran-2-yl group or a group —OCO—O—lower alkyl, by a Wittig reaction and subsequent cleavage of the protecting group. Compounds of formula VI in which Z is a SH group can be prepared from compounds of formula II by reaction with S-(4-formylphenyl)-dimethyl- thiocarbamate (see Ep 58370 B1) and subsequent cleavage of the thiocarbamate group by treatment with LiAlH$_4$.

Compounds of formula VI in which Z is a residue —NHR$^9$ can be obtained by preparing a compound corresponding to formula VI with Z=NO$_2$ from a compound of formula II and p-nitrobenzaldehyde by a Wittig reaction, whereupon the nitro group is reduced, e.g. with Na$_2$S$_2$O$_4$ or nascent hydrogen, to the amino group which is finally alkylated or acylated to the group —NHR$^9$.

Compounds of formula VI in which Z is a residue —SO$_2$$^-$M$^+$ can be prepared as described in European patent Specification 58370.

The biological activity of the compounds in accordance with the invention can be determined e.g. using the test procedures described in German Offenlegungsschrift 3 715 955. In testing the activity against chemically induced (oral administration of dimethylbenzanthracene) mammary tumours in rats the results compiled hereinafter were obtained with the compound of formula I, 4-[2-[p-[(E)-2-(5,6,7,8-tetrahydro-5,5,8,8-tetramethyl-2-naphthyl)propenyl]phenoxy]ethyl]morpholine:

|  | Dosage [mg/kg/day] p.o. | Rats with tumours [% of controls] | Increase or decrease in the average number of tumours per rat | Increase or decrease in the average tumour volume per rat in mm$^3$ |
|---|---|---|---|---|
|  | 50 | 100 | +91 | +550 |
|  | 100 | 50 | −73 | −77 |
|  | 200 | 10 | −96 | −99 |
| Control group | — | 100 | +242 | +714 |

The compounds of formula I can be used for the topical and systemic therapy of benign and malignant neoplasms, of premalignant lesions as well as, further, for the systemic and topical prophylaxis of the said conditions.

Furthermore, they are suitable for the topical and systemic therapy of acne, psoriasis and other dermatoses which are accompanied by an intensified or pathologically altered cornification, as well as of inflammatory and allergic dermatological conditions. Further, the compounds of formula I can also be used for the control of mucous membrane disorders with inflammatory or degenerative or metaplastic changes. Furthermore, the compounds of formula I can be used, preferably in topical preparations, for the treatment and prophylaxis of light-damaged skin (ageing of the skin).

The compositions can be administered enterally, parenterally or topically. For enteral administration there are suitable e.g. compositions in the form of tablets, capsules, dragees, syrups, suspensions, solutions and suppositories. Preparations in the form of infusion or injection solutions are suitable for parenteral administration.

The dosages in which the preparations are administered can vary according to the mode of use and route of use as well as according to the requirements of the patients. In general, daily dosages of about 0.1–100 mg/kg, preferably 1–50 mg/kg, come into consideration for adults.

The preparations can contain inert or pharmacodynamially active additives. Tablets or granulates e.g. can contain a series of binding agents, filler materials, carrier substances or diluents. Liquid preparations can be present, for example, in the form of a sterile solution which is miscible with water. Capsules can contain a filler material or thickening agent in addition to the active substance. Furthermore, there can also be present flavour-improving additives as well as the substances usually used as preserving, stabilizing, moistureretaining and emulsifying agents, salts for varying the osmotic pressure, buffers and other additives.

The previously mentioned carrier substances and diluents can consist of organic or inorganic substances, e.g. of water, gelatine, lactose, starch, magnesium stearate, talc, gum arabic, polyalkylene glycols and the like. It is a prerequisite that all adjuvants used in the manufacture of the preparations are non-toxic.

For topical use the active substances are conveniently used in the form of salves, tinctures, creams, solutions, lotions, sprays, suspensions and the like. Salves and creams as well as solutions are preferred. These preparations intended for topical use can be manufactured by mixing compounds of formula I as active ingredients with non-toxic, inert, solid or liquid carriers which are usual in such preparations and which are suitable for topical treatment.

For topical use there are suitable compositions which can conveniently comprise active ingredient in the following ranges by weight per cent. For solutions, about 0.1–5%, preferably 0.3–2%. For salves or creams about 0.1–5%, preferably about 0.3–2%.

If desired, an antioxidant, e.g. tocopherol, N-methyl-q-tocopheramine as well as butylated hydroxyanisole or butylated hydroxytoluene, can be admixed with the preparations.

The following Examples illustrate the invention further. The temperatures are given in degrees Celsius.

EXAMPLE 1

332 g of 2-[(5,6,7,8-tetrahydro-5,5,8,8-tetramethyl-2-naphthyl)ethyl]triphenylphosphonium bromide are suspended in 1.2 l of tetrahydrofuran. 406 ml of butyllithium (1.6 molar in hexane) are added dropwise thereto at 0° while stirring. After stirring at 0° for 1 hour a solution of 120 g of 4-(2-morpholinoethoxy)benzaldehyde in 400 ml of tetrahydrofuran is added dropwise to the dark red solution. After stirring at room temperature for 2 hours the reaction mixture is poured into 3 l of a methanol/water mixture (6:4) and extracted with hexane. The organic phase is washed with water, dried over sodium sulphate and evaporated. The yellowish, crystalline residue is recrystallized from ethyl acetate/hexane and gives 123 g of 4-[2-[p-[(E)-2-(5,6,7,8-tetrahydro-5,5,8,8-tetramethyl-2-naphthyl)propenyl]phenoxy]ethyl]morpholine in white crystals, melting point 107°–109°.

The 4-(2-morpholinoethoxy)benzaldehyde used as the starting material can be prepared as follows:

92.8 g of 4-hydroxybenzaldehyde are dissolved in 820 ml of dimethylformamide. After the addition of 228 g of 4-(2-chloroethyl)morpholine and 415 g of finely powdered potassium carbonate the reaction mixture is heated to 100° overnight under argon and while stirring vigorously. The cooled solution is poured into 3 l of ice-water, extracted with ethyl acetate, washed with water, dried and evaporated. The residual dark oil is distilled in a high vacuum and gives 132 g of 4-(2-morpholinoethoxy)benzaldehyde as a yellowish oil, boiling point 145°–150°/33 pa.

EXAMPLE 2

In a manner analogous to Example 1, from 26 g of triphenyl [1-(1,1,3,3-tetramethyl-5-indenyl)ethyl]-phosphonium bromide and 10 g of 4-(2-morpholinoethoxy)-benzaldehyde there are obtained, after recrystallization from hexane, 13.6 g of 4-[2-[p-[(E)-2-(1,1,3,3-tetramethyl-5-indenyl)propenyl]phenoxy]ethyl]morpholine in white crystals, melting point 85°–86°.

EXAMPLE 3

0.75 g of a 50% suspension of sodium hydride in mineral oil is suspended in 10 ml of dimethylformamide. A solution of 5 g of p-[(E)-2-(5,6,7,8-tetrahydro-5,5,8,-tetramethyl-2-naphthyl)propenyl]phenol in 30 ml of dimethylformamide is added dropwise thereto while stirring at 0°. After stirring at 0° for 1 hour a solution of 3.6 g of N-(2-chloroethyl)pyrrolidine in 30 ml of dimethylformamide is added dropwise thereto. The reaction mixture is subsequently heated to 70° for 2 hours, thereafter cooled, poured into ice-water and extracted with ethyl acetate. The organic solution is washed several times with water, dried and evaporated. There is obtained a yellow-brown oil which is purified by filtration over silica gel (eluting agent ethyl acetate +10% ethanol) and recrystallized from hexane. There are isolated 4.5 g of 1-[p-[2-[2-(5,6,7,8-tetrahydro-5,5,8,8-tetramethyl-2-naphthyl)propenyl]phenoxy]ethyl]pyrrolidine in white crystals, melting point 80°–82°.

EXAMPLE 4

In a manner analogous to Example 3, from 5 g of p-[(E)-2-(5,6,7,8-tetrahydro-5,5,8,8-tetramethyl-2-naphthyl)propenyl]phenol and 4.7 g of 1-(2-chloroethyl)-piperidine there are obtained 5.2 g of 1-[2-[p-[(E)-2-(5,6,7,8-tetrahydro-5,5,8,8-tetramethyl-2-naphthyl)-propenyl]phenoxy]ethyl]piperidine in white crystals, melting point 91°–93°.

EXAMPLE 5

A mixture of 6 g of p-[(E)-2-(5,6,7,8-tetrahydro-5,5,8,8-tetramethyl-2-naphthyl)propenyl]phenol, 4.8 g of 2-chloroethyl methyl sulphide and 10.5 g finely powdered potassium carbonate in 100 ml of dimethylformamide is heated to 100° for 20 hours. The cooled reaction mixture is diluted with water and extracted several times with ethyl acetate. The crystalline residue obtained after drying and evaporating the organic phase is recrystallized from hexane and gives 5.5 g of methyl 2-[p-[(E)-2-( 5,6,7,8-tetrahydro-5,5,8,8-tetramethyl-2-naphthyl)-propenyl]phenoxy]ethyl sulphide in colourless crystals, melting point 94°–96°.

EXAMPLE 6

2.1 g of the compound obtained in Example 5 are dissolved in 50 ml of chloroform and treated slowly at 0° with a solution of 1.2 g of m-chloroperbenzoic acid (90%) in 10 ml of chloroform. After stirring at 0° for 20 hours the mixture is washed with dilute soda solution and water, dried and evaporated. The thus-obtained yellow oil is filtered over a small silica gel column (eluting agent hexane/ethyl acetate =1:2) and recrystallized from ethyl acetate. There are obtained 1.7 g of methyl 2-[p-[(E)-2-(5,6,7,8-tetrahydro-5,5,8,8-tetramethyl-2-naphthyl)-propenyl]phenoxy]ethyl sulphoxide, melting point 134°–136°.

EXAMPLE 7

In analogy to Example 6, from 2.8 g of methyl 2-[p-[(E)-2-(5,6,7,8-tetrahydro-5,5,8,8-tetramethyl-2-naphthyl)propenyl]phenoxy]ethyl sulphide and 3.1 g of m-chloroperbenzoic acid (90%) there are obtained, after filtration of the crude product over a small silica gel column (eluting agent hexane/ethyl acetate =1:1) and recrystallization from ethyl acetate, 1.7 g of methyl 2-[p-[(E)-2-(5,6,7,8-tetrahydro-5,5,8,8-tetramethyl-2-naphthyl)propenyl]phenoxy]ethyl sulphone, melting point 169°–171°.

EXAMPLE 8

In analogy to Example 5, from 8.2 g of p-[(E)-2-(5,6,7,8-tetrahydro-5,5,8,8-tetramethyl 2-naphthyl)-propenyl]thiophenol, 12 g of 1-chloro-2-dimethylamino-ethane and 6.9 g of potassium carbonate by heating to 60° in dimethylformamide there are obtained, after recrystallization from hexane, 3.5 g of N,N-dimethyl-2-[[p-[(E)-2-(5,6,7,8-tetrahydro-5,5,8,8-tetramethyl-2-naphthyl)propenyl]phenyl]thio]ethylamine, melting point 57°–59°.

EXAMPLE 9

In analogy to Example 8, from 8.2 g of p-[(E)-2-(5,6,7,8-tetrahydro-5,5,8,8-tetramethyl-2-naphthyl)-propenyl]thiophenol, 10.6 g of 2-chloroethyl methyl ether and 6.9 g of potassium carbonate there are obtained, after recrystallization from hexane, 5 of 2-methoxyethyl p-[(E)-2-(5,6,7,8-tetrahydro-5,5,8,8-tetramethyl-2-naphthyl)propenyl]phenyl sulphide, melting point 48°–50°.

EXAMPLE 10

In analogy to Example 8, from 8.2 g of p-[(E)-2-(5,6,7,8-tetrahydro-5,5,8,8-tetramethyl-2-naphthyl)-propenyl]thiophenol, 12.4 g of 2-chloroethyl methyl sulphide and 6.9 g of potassium carbonate there are obtained, after recrystallization from hexane, 3.5 g of 2-thiomethoxyethyl p-[(E)-2-(5,6,7,8-tetrahydro-5,5,8,8-tetramethyl-2-naphthyl)propenyl]phenyl sulphide, melting point 65°–67°.

EXAMPLE 11

3 g of sodium p-[2-(5,6,7,8-tetrahydro-5,5,8,8-tetramethyl-2-naphthyl)propenyl]phenyl sulphinate are suspended in 30 ml of dimethylformamide and treated with 1.5 g of 2-chloroethyl methyl ether. After heating to 90° for 20 hours the mixture is diluted with water, extracted with ethyl acetate, dried and evaporated. The crude product is filtered over a silica gel column (eluting agent hexane/ethyl acetate =4:1) and gives, after recrystallization from hexane/ether, 1.8 g of 2-methoxyethyl p-[(E)-2-[5,6,7,8-tetrahydro-5,5,8,8-tetramethyl-2-naphthyl]propenyl]phenyl sulphone, melting point 104°–106°.

EXAMPLE 12

In analogy to Example 1, from 38.5 g of [1-(5,6,7,8-tetrahydro-5,5,8,8-tetramethyl-2-naphthyl)ethyl]triphenylphosphonium bromide, 45 ml of butyllithium and 13.7 g of p-[[2-(dimethylamino)ethyl]methylamino]benzaldehyde there are obtained, after filtration over silica gel (eluting agent ethyl acetate, then ethyl acetate/ethanol = 1:1 with the addition of 1% triethylamine) and recrystallization from hexane, 9.2 g of N,N,N'-trimethyl—N-[p-[(E)-2-(5,6,7,8-tetrahydro-5,5,8,8-tetramethyl-2-naphthyl)propenyl]phenyl]ethylenediamine, melting point 46°–48°.

The p-[[2-(dimethylamino)ethyl]methylamino]benzaldehyde used as the starting material can be prepared as follows:

A mixture of 10 g of 4-fluorobenzaldehyde, 9.7 g of trimethylethylenediamine and 13.1 g of potassium carbonate in 20 ml of dimethylformamide is heated to 150° for 16 hours. After cooling the mixture is diluted with water and extracted with ethyl acetate. The organic phase is washed several times with water, dried and evaporated. The brownish oil (13.7 g) is dried in a high vacuum and is used without further purification.

EXAMPLE 13

In analogy to Example 12, from 10.4 g of [1-(5,6,7,8-tetrahydro-5,5,8,8-tetramethyl-2-naphthyl)ethyl]triphenylphosphonium bromide, 12.2 ml of butyllithium and 3.4 g of p-[[2-(dimethylamino)ethyl]amino]benzaldehyde there are obtained, after recrystallization from hexane/ethyl acetate, 2 g of N,N-dimethyl—N'-[p-[(E)-2-(5,6,7,8-tetrahydro-5,5,8,8-tetramethyl-2-naphthyl)propenyl]phenyl]ethylenediamine, melting point 102°–104°.

The p-[2-(dimethylamino)ethyl]amino]benzaldehyde used as the starting material can be prepared as described in Example 12 as a brownish oil from 4-fluorobenzaldehyde and 2-dimethylaminoethylamine.

EXAMPLE 14

2.1 g of [1-(6,7,8,9-tetrahydro-7,7-dimethyl-5H-benzocyclohepten-2-yl)ethyl]triphenylphosphonium bromide are suspended in 10 ml of toluene and treated at 0° with 0.5 g of potassium tert-butylate. After stirring at room temperature for 2 hours a solution of 0.94 g of 4-(2-morpholinoethoxy)benzaldehyde in 5 ml of toluene is added dropwise thereto and the mixture is stirred at room temperature for 3 hours. After evaporating the majority of the solvent the residue is poured into a mixture of methanol/water (6:4) and extracted several times with hexane. The organic phase is washed with water, dried and evaporated. Recrystallization of the residue from hexane gives 0.4 g of 4-[2-[p-[(E)-2-(6,7,8,9-tetrahydro-7,7-dimethyl-5H-benzocyclohepten-2-yl)propenyl]phenoxy]ethyl]morpholine, melting point 78°–79°.

EXAMPLE 15

In analogy to Example 1, from 22 g of 2-[(5,6,7,8-tetrahydro-5,5,8,8-tetramethyl-2-naphthyl)ethyl]triphenylphosphonium bromide and 9.5 g of p-[[2-morpholino)ethyl]methylamino]benzaldehyde there are obtained, after recrystallization from hexane, 7 g of 4-[2-[N-methyl-p-[ (E)-2-(5,6,7,8-tetrahydro-5,5,8,8-tetramethyl-2-naphthyl)propenyl]anilino]ethyl]morpholine, melting point 86°–88°, in white crystals.

The p-[[2-morpholino)ethyl]methylamino]benzaldehyde used as the starting material can be prepared as described in Example 12 as a brownish oil, which crystallizes in the cold, from 4-fluorobenzaldehyde and 4-[2-(N-methylamino)ethyl]morpholine.

EXAMPLE 16

Analogously to Example 1, from b 2-[(5,6,7,8-tetrahydro-5,5,8,8-tetramethyl-2-naphthyl)ethyl]triphenylphosphonium bromide and 4-[2-(tetrahydro-4'H-1,4-thiazin-4'-yl)ethoxy]benzaldehyde 1',1'-dioxide there is obtained, after stirring at room temperature for 16 hours, working-up, flash chromatography on silica gel with hexane/ethyl acetate (1:2) and crystallization from ethyl acetate/hexane, tetrahydro-4-[2-[p-[(E)-2-(5,6,7,8-tetrahydro-5,5,8,8-tetramethyl-2-naphthyl)propenyl]phenoxy]ethyl]-2H-1,4-thiazine 1,1-dioxide of melting point 144°–145°.

The 4-[2-(tetrahydro-4'H-1,4-thiazin-4'-yl)ethoxy]benzaldehyde 1',1'-dioxide can be prepared as follows:

11.6 g of 4-hydroxybenzaldehyde in 160 ml of dimethylformamide are heated to 100° under argon for 2 hours with 15.6 g of 4-(2-chloroethyl)-tetrahydro-2H-1,4-thiazine 1,1-dioxide and 21.6 g of powdered potassium carbonate. After cooling the mixture is poured on to 150 g of ice, extracted three times with 300 ml of ethyl acetate and the organic phases are washed twice with 150 ml of water, dried over sodium sulphate and evaporated in a vacuum. The beige, crystalline residue (22.1 g) is used directly for the above Wittig reaction. A sample was chromatographed on silica gel with ethyl acetate/hexane (4:1) and yielded colourless crystals of melting point 101°-102° from ethyl acetate/hexane.

The manufacture of dosage forms containing the compounds of formula I can be effected in the usual manner, e.g. on the basis of the following Examples.

EXAMPLE A

Hard gelatine capsules can be manufactured as follows:

| Ingredients | mg/capsule |
|---|---|
| 1. Spray-dried powder containing 75% of compound of formula I | 200 |
| 2. Sodium dioctylsulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 300 |

The spray-dried powder, which is based on the active substance, gelatine and microcrystalline cellulose and which has an average particle size of the active substance of <1 m (measured by means of autocorrelation spectroscopy), is moistened with an aqueous solution of sodium carboxymethylcellulose and sodium dioctylsulphosuccinate and kneaded. The resulting mass is granulated, dried and sieved, and the granulate obtained is mixed with micro-crystalline cellulose, talc and magnesium stearate. The powder is filled into size 0 capsules.

EXAMPLE B

Tablets can be manufactured as follows:

| Ingredients | mg/tablet |
|---|---|
| 1. Compound of formula I as a finely milled powder | 500 |
| 2. Lactose powder | 100 |
| 3. Maize starch white | 60 |
| 4. Povidone K30 | 8 |
| 5. Maize starch white | 112 |
| 6. Talc | 16 |
| 7. Magnesium stearate | 4 |
| Total | 800 |

The finely milled substance is mixed with lactose and a portion of the maize starch. The mixture is moistened with an aqueous solution of Providone K30 (polyvinyl pyrrolidone, average molecular weight about 40,000) and kneaded, and the resulting mass is granulated, dried and sieved. The granulate is mixed with the remaining maize starch, talc and magnesium stearate and pressed to tablets of suitable size.

EXAMPLE C

Soft gelatine capsules can be manufactured as follows:

| Ingredients | mg/capsule |
|---|---|
| 1. Compound of formula I | 50 |
| 2. Triglyceride | 450 |
| Total | 500 |

10 g of compound of formula I are dissolved in 90 g of medium-chain triglyceride with stirring, inert gasification and protection from light. This solution is processed as the capsule fill mass to soft gelatine capsules containing 50 mg of active substance.

EXAMPLE D

A lotion can be manufactured as follows:

| Ingredients | |
|---|---|
| 1. Compound of formula I, finely milled | 3.0 g |
| 2. Carbopol 934 | 9.6 g |
| 3. Sodium hydroxide | q.s. ad pH 6 |
| 4. Ethanol, 94% | 50.0 g |
| 5. Demineralized water | ad 100.0 g |

The active substance is incorporated into the ethanol, 94%/water mixture under protection from light. Carbopol 934 (a crosslinked polymer of acrylic acid of average molecular weight of about 3,000,000) is stirred in until gelling is complete and the pH value is adjusted with sodium hydroxide.

We claim:

1. A compound of the formula

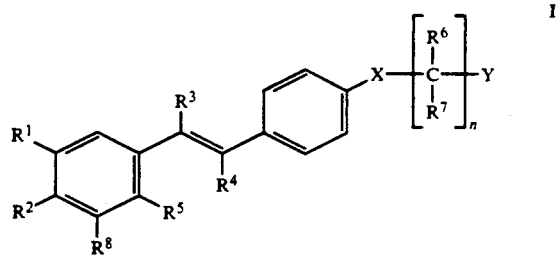

wherein $R^1$ and $R^2$ each independently is lower-alkyl; or together are alkylene with 3-5 C-atoms in a straight chain; or together are alkylene with 3-5 C-atoms in a straight chain wherein said alkylene is lower-alkyl substituted; one of the residues $R^3$ and $R^4$ is hydrogen and the other is hydrogen or lower-alkyl; $R^6$ and $R^7$ are hydrogen or loweralkyl; $R^5$ and $R^8$ are hydrogen, lower-alkyl, lower-alkoxy or halogen; X is —O—, —S—, —SO—, —SO$_2$—, or —NR$^9$; $R^9$ is hydrogen, lower-alkyl or acyl; Y is piperidino attached via the N-atom; and n is 2, 3 or 4.

2. A compound in accordance with claim 1, wherein $R^1$ and $R^2$ together are a residue —(CH$_3$)$_2$C—CH$_2$CH$_2$C(CH$_3$)$_2$— or —(CH$_3$)$_2$C—CH$_2$—C(CH$_3$)$_2$—.

3. A compound in accordance with claim 2, wherein X is —O—.

4. A compound in accordance with claim 2, wherein X is —S—, —SO—, SO$_2$— or —NR$^9$—.

5. A compound in accordance with claim 1, wherein $R^1$ and $R^8$ are lower-alkyl.

6. The compound in accordance with claim 1, 1-[2-[p-[(E)-2-(5,6,7,8-tetrahydro-5,5,8,8-tetramethyl-2-naphthyl)propenyl]phenoxy]ethyl]piperidine.

7. A pharmaceutical composition comprising an effective amount of a compound of the formula

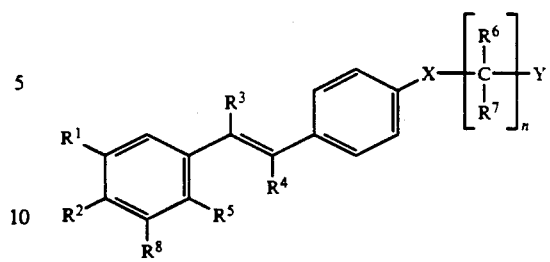

wherein $R^1$ and $R^2$ each independently is lower-alkyl; or together are alkylene with 3-5 C-atoms in a straight chain; or together are alkylene with 3-5 C-atoms in a straight chain wherein said alkylene is lower-alkyl substituted; one of the residues $R^3$ and $R^4$ is hydrogen and the other is hydrogen or lower-alkyl; $R^6$ and $R^7$ are hydrogen or lower-alkyl; $R^5$ and $R^8$ are hydrogen, lower-alkyl, lower-alkoxy or halogen; X is —O—, —S—, —SO—, —SO$_2$—, or —NR$^9$; $R^9$ is hydrogen, lower-alkyl or acyl; Y is piperidino attached via a N-atom; and n is 2, 3 or 4, and a pharmaceutically inert carrier material.

* * * * *